United States Patent
Chennubhotla et al.

(10) Patent No.: US 12,033,726 B2
(45) Date of Patent: Jul. 9, 2024

(54) SPATIALLY CO-REGISTERED GENOMIC AND IMAGING (SCORGI) DATA ELEMENTS FOR FINGERPRINTING MICRODOMAINS

(71) Applicant: UNIVERSITY OF PITTSBURGH-OF THE COMMONWEALTH SYSTEM OF HIGHER EDUCATION, Pittsburgh, PA (US)

(72) Inventors: Srinivas C. Chennubhotla, Pittsburgh, PA (US); Albert H. Gough, Glenshaw, PA (US); Andrew M. Stern, Pittsburgh, PA (US); Michael J. Becich, Wexford, PA (US); Douglass L Taylor, Pittsburgh, PA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 746 days.

(21) Appl. No.: 17/265,954

(22) PCT Filed: Aug. 21, 2019

(86) PCT No.: PCT/US2019/047412
§ 371 (c)(1),
(2) Date: Feb. 4, 2021

(87) PCT Pub. No.: WO2020/046661
PCT Pub. Date: Mar. 5, 2020

(65) Prior Publication Data
US 2021/0383894 A1    Dec. 9, 2021

Related U.S. Application Data

(60) Provisional application No. 62/721,018, filed on Aug. 22, 2018.

(51) Int. Cl.
*G16B 40/10* (2019.01)
*B01L 3/00* (2006.01)
(Continued)

(52) U.S. Cl.
CPC ............ *G16B 40/10* (2019.02); *B01L 3/5085* (2013.01); *G01N 1/2806* (2013.01); *G01N 1/30* (2013.01);
(Continued)

(58) Field of Classification Search
CPC ..... G16B 40/10; B01L 3/5085; G01N 1/2806; G01N 1/30; G01N 1/06; G06F 3/04817;
(Continued)

(56) References Cited

U.S. PATENT DOCUMENTS

| | | | |
|---|---|---|---|
| 2002/0048766 A1* | 4/2002 | Doyle | C12Q 1/6841 435/6.12 |
| 2003/0215936 A1 | 11/2003 | Kallioniemi et al. | |

(Continued)

FOREIGN PATENT DOCUMENTS

| | | | | |
|---|---|---|---|---|
| WO | 01/142796 A1 | 6/2001 | | |
| WO | WO-0142796 A1 * | 6/2001 | ............. | G01N 1/312 |

(Continued)

OTHER PUBLICATIONS

Chennubhotla, C et al., Informatics Tools for Tumor Heterogeneity in Multiplexed Fluorescence Images. National Cancer Institute Center for Biomedical Informatics and Information Technology. Jun. 13, 2017; retrieved from the Internet <https://ncihub.org/groups/itcr/collections/itcr-2017-annual-pi-meeting>; pp. 1-32; pp. 15-17, 24-25.

*Primary Examiner* — Bobbak Safaipour
*Assistant Examiner* — Jongbong Nah
(74) *Attorney, Agent, or Firm* — Philip E. Levy; Eckert Seamans Cherin & Mellott, LLC (57) ABSTRACT

A method of generating a plurality of spatially co-registered data elements, each spatially co-registered data element
(Continued)

being associated with and generated from a pair of co-registered tissue sections obtained from adjacent positions of a core taken from a tissue sample and including an image data section and a genomic data section. The method includes, for each pair of co-registered tissue sections: (i) obtaining and storing as part of a data element a plurality of multi to hyperplexed images from the imaging data section of the co-registered tissue section, (ii) generating and storing as part of the data element image data from the plurality of multi to hyperplexed images, and (iii) generating and storing as part of the data element genomic data from the genomic data section of the associated co-registered tissue section.

24 Claims, 6 Drawing Sheets (51) Int. Cl.
  *G01N 1/28* (2006.01)
  *G01N 1/30* (2006.01)
  *G06F 3/0481* (2022.01)
  *G06F 3/04817* (2022.01)
  *G06F 3/0482* (2013.01)
  *G06T 7/00* (2017.01)

(52) U.S. Cl.
  CPC ........ *G06F 3/04817* (2013.01); *G06F 3/0482* (2013.01); *G06T 7/0012* (2013.01); *G06T 2200/24* (2013.01); *G06T 2207/30024* (2013.01); *G06T 2207/30072* (2013.01); *G06T 2207/30096* (2013.01)

(58) Field of Classification Search
  CPC . G06F 3/0482; G06T 7/0012; G06T 2200/24; G06T 2207/30024; G06T 2207/30072; G06T 2207/30096
  See application file for complete search history.

(56) References Cited

U.S. PATENT DOCUMENTS

| 2009/0247416 | A1 | 10/2009 | Can et al. | |
|---|---|---|---|---|
| 2013/0225655 | A1* | 8/2013 | Lu | ........................ A61K 31/713 |
| | | | | 514/44 A |
| 2017/0011511 | A1* | 1/2017 | Goodman | .............. G06V 10/24 |

FOREIGN PATENT DOCUMENTS

| WO | 2003044213 A2 | 5/2003 | | |
|---|---|---|---|---|
| WO | WO-03044213 A2 * | 5/2003 | .............. | G01N 1/36 |
| WO | 2008008500 A2 | 1/2008 | | |

* cited by examiner

SPATIALLY CO-REGISTERED GENOMIC AND IMAGING (SCORGI) DATA ELEMENTS FOR FINGERPRINTING MICRODOMAINS

CROSS-REFERENCE TO RELATED APPLICATIONS

This application is a U.S. National Stage Application under 35 U.S.C. § 371 of PCT International Application No. PCT/US2019/047412, filed on Aug. 21, 2019, entitled, "Spatially Co-Registered Genomic and Imaging (Scorgi) Data Elements for Fingerprinting Microdomains," which claims priority under 35 U.S.C. § 119(e) from U.S. provisional patent application No. 62/721,018, filed on Aug. 22, 2018, entitled "Spatially CO-Registered Genomic and Imaging (SCORGI) Data Elements for Fingerprinting Microdomains", the disclosure of which is incorporated herein by reference.

GOVERNMENT CONTRACT

This invention was made with government support under grant number CA204826 awarded by the National Institutes of Health (NIH). The government has certain rights in the invention.

BACKGROUND OF THE INVENTION

1. Field of the Invention

The present invention pertains to digital pathology, and in particular, to a method for creating spatially co-registered genomic and imaging (SCORGI) data elements for fingerprinting microdomains from tumors and/or related tissue, including a new tumor sampling strategy for characterizing spatial heterogeneity in solid tumors, and to digital pathology systems employing same.

2. Description of the Related Art

Digital pathology refers to the acquisition, storage and display of histologically stained tissue samples and is initially gaining traction in niche applications such as second-opinion telepathology, immunostain interpretation, and intraoperative telepathology. Typically, a large volume of patient data, consisting of 3-50 slides, is generated from biopsy samples and is visually evaluated by a pathologist, under a microscope, but with digital technology by viewing on a high-definition monitor. Because of the manual labor involved, the current workflow practices are time consuming, error-prone and subjective.

Cancer is a heterogeneous disease. In hematoxylin and eosin (H&E) stained tissue images, heterogeneity is characterized by the presence of various histological structures, such as carcinoma in situ, invasive carcinoma, adipose tissue, blood vessels, and normal ducts. Moreover, for many malignancies, molecular and cellular heterogeneity is a prominent feature among tumors from different patients, between different sites of neoplasia in a single patient, and within a single tumor. Intratumor heterogeneity involves phenotypically distinct cancer cell clonal subpopulations and other cell types that comprise the tumor microenvironment (TME). These cancer cell clonal subpopulations and other cell types include local and bone marrow derived stromal stem and progenitor cells, subclasses of immune inflammatory cells that are either tumor promoting or tumor-killing, cancer associated fibroblasts, endothelial cells and pericytes. The TME can be viewed as an evolving ecosystem where cancer cells engage in heterotypic interactions with these other cell types and use available resources to proliferate and survive. Consistent with this perspective, the spatial relationships among the cell types within the TME (i.e., spatial heterogeneity) appear to be one of the main drivers of disease progression and therapy resistance. Thus, it is imperative to define the spatial heterogeneity within the TME to properly diagnose the specific disease sub-type and identify the optimal course of therapy for individual patients.

To date, intratumor heterogeneity has been explored using three major approaches. The first approach is to take core samples from specific regions of tumors to measure population averages. Heterogeneity in the samples is measured by analyzing multiple cores within the tumor using a number of techniques, including whole exome sequencing, epigenetics, proteomics, and metabolomics. The second approach involves "single cell analyses" using the above methods, RNASeq, imaging or flow cytometry after separation of the cells from the tissue. The third approach uses the spatial resolution of light microscope imaging to maintain spatial context, and is coupled with molecular-specific labels to measure biomarkers in the cells in situ. These approaches, while each providing a certain level of effectiveness, all have various drawbacks and limitations.

In addition, one of the biggest challenges in assessing the clinical significance of tumor heterogeneity has been the lack of tools for spatial analysis of samples at the single cell level, combined with limited tools for integration of genomic and proteomic measurements in appropriate clinically- and molecularly-annotated sample sets.

There is thus room for improvement in the field of intratumor heterogeneity characterization.

SUMMARY OF THE INVENTION

In one embodiment, a method of creating a plurality of tissue sections for imaging and genomic analysis is provided. The method includes obtaining a number of cores from a tissue sample, and, for each core, obtaining from the core a plurality of imaging data sections and a plurality of genomic data sections in an alternating fashion along a length of the core such that each of the imaging data sections is associated with a respective one of the genomic data sections to form a plurality of serial pairs of adjacent tissue sections.

In another embodiment, a plurality of tissue microarray (TMA) slides including tissue sections for imaging and genomic analysis is provided. The plurality of TMA slides includes a number of first TMA slides having fixed thereto a plurality of imaging data sections for each of a number of cores from a tissue sample, and a number of second TMA slides having fixed thereto a plurality of genomic data sections for each of the number of cores from the tissue sample. For each core, the plurality of imaging data sections and the plurality of genomic data sections come from alternating portions along a length of the core such that each of the imaging data sections is associated with a respective one of the genomic data sections for the core to form a plurality of serial pairs of adjacent tissue sections.

In still another embodiment, a method of generating a plurality of spatially co-registered data elements from a tissue sample is provided. The method includes obtaining a number of cores from the tissue sample, and, for each core, obtaining from the core a plurality of imaging data sections and a plurality of genomic data sections in an alternating fashion along a length of the core such that each of the imaging data sections is associated with a respective one of the genomic data sections to form a plurality of serial pairs of adjacent, co-registered tissue sections. The method further includes for each of the imaging data sections: (i) obtaining a plurality of multi to hyperplexed images by repeated labeling with a plurality of fluorescent tags, (ii) analyzing the multi to hyperplexed images to obtain image data therefrom, and (iii) identifying a number of regions of interest in the genomic data section associated with the imaging data section based on the obtained image data for the imaging data section. The method also further includes for each genomic data section, performing genomic analysis on each of the regions of interest in the genomic data section to generate genomic data for the genomic data section, and for each co-registered tissue section, associating with one another as a co-registered imaging and genomic data element: (i) the multi to hyperplexed images of the imaging data section of the co-registered tissue section, (ii) the image data of the imaging data section of the co-registered tissue section, and (iii) genomic data of the genomic data section of the co-registered tissue section.

In yet another embodiment, a non-transitory computer readable medium storing a plurality of spatially co-registered data elements is provided. Each spatially co-registered data element being associated with and generated from a pair of co-registered tissue sections obtained from adjacent positions of a core taken from a tissue sample and including an image data section and a genomic data section, each spatially co-registered data element comprising: (i) a plurality of multi to hyperplexed images obtained from the imaging data section of the associated pair of co-registered tissue sections, (ii) image data generated from the plurality of multi to hyperplexed images obtained from the imaging data section of the associated pair of co-registered tissue sections, and (iii) genomic data generated from the genomic data section of the associated pair of co-registered tissue sections.

In another embodiment, a method of generating a plurality of spatially co-registered data elements, each spatially co-registered data element being associated with and generated from a pair of co-registered tissue sections obtained from adjacent positions of a core taken from a tissue sample and including an image data section and a genomic data section, is provided. The method includes, for each pair of co-registered tissue sections: (i) obtaining and storing as part of a data element a plurality of multi to hyperplexed images from the imaging data section of the co-registered tissue section, (ii) generating and storing as part of the data element image data from the plurality of multi to hyperplexed images, and (iii) generating and storing as part of the data element genomic data from the genomic data section of the associated co-registered tissue section.

In yet another embodiment, a system for generating and storing a spatially co-registered data element is provided. The spatially co-registered data element is associated with and generated from a pair of co-registered tissue sections obtained from adjacent positions of a core taken from a tissue sample, the pair of co-registered tissue sections including an image data section and a genomic data section. The system comprises a processing apparatus that includes (i) an image data generation component that is structured and configured to generate image data from a plurality of multi to hyperplexed images obtained from the imaging data section of the associated pair of co-registered tissue sections; (ii) a region of interest identification component that is structured and configured to identify a number of regions of interest in the genomic data section of the associated pair of co-registered tissue sections based on the generated image data, wherein genomic data is generated from the genomic data section of the associated co-registered tissue section based on the identified number of regions of interest; and (iii) data element generation component that is structured and configured to generate and store the spatially co-registered data element, the spatially co-registered data element including the plurality of multi to hyperplexed images, the generated image data, and the generated genomic data.

DETAILED DESCRIPTION OF EXEMPLARY EMBODIMENTS

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

As used herein, the term "multiplexed imaging" shall refer to imaging techniques that employ up to 7 biomarkers, and "multiplexed images" shall to refer to images created using multiplexed imaging.

As used herein, the term "hyperplexed imaging" shall refer to imaging techniques that employ greater than 7 biomarkers, and "hyperplexed images" shall to refer to images created using hyperplexed imaging.

As used herein, the term "multi to hyperplexed imaging" shall include multiplexed imaging and/or hyperplexed imaging, and "multi to hyperplexed images" shall include multiplexed images and/or hyperplexed images.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

The disclosed concept, in once aspect, provides a new tumor sampling strategy for characterizing spatial heterogeneity in solid tumors that is based on what the present inventors refer to as "SCORGIs." As described in greater detail herein, SCORGIs are spatially co-registered genomic and imaging data elements that are generated from spatially co-registered adjacent tissue samples obtained from, for example and without limitation, matched primary tumors, regional lymph nodes and distal metastases. SCORGIs integrate region specific genomic information (such as, without limitation, whole-exome sequencing acquired via next generation sequencing methods, in situ transcriptomics, and epigenomics, among others) and imaging information (e.g., without limitation, acquired via extensive fluorescently labeled antibody biomarkers) obtained from a large number of individual sample cores distributed within such tissue samples. The unprecedented SCORGI based tumor sampling strategy of the disclosed concept enables digital fingerprinting of microdomains that represent spatial, functional, and genomic intra-tumor heterogeneity (ITH) among malignant cells, non-malignant cells (e.g., without limitation, immune cells, cancer associated fibroblasts (CAFs), and endothelial cells), and their localized interactions within the tumor microenvironment (TME) that is believed to be a critical determinant of metastatic disease progression. Additionally, the SCORGI based digital fingerprinting of microdomains according to the disclosed concept will enable the identification and characterization of pathogenic signaling networks within the TME, potentially leading to improved therapeutic strategies.

Figure 1:
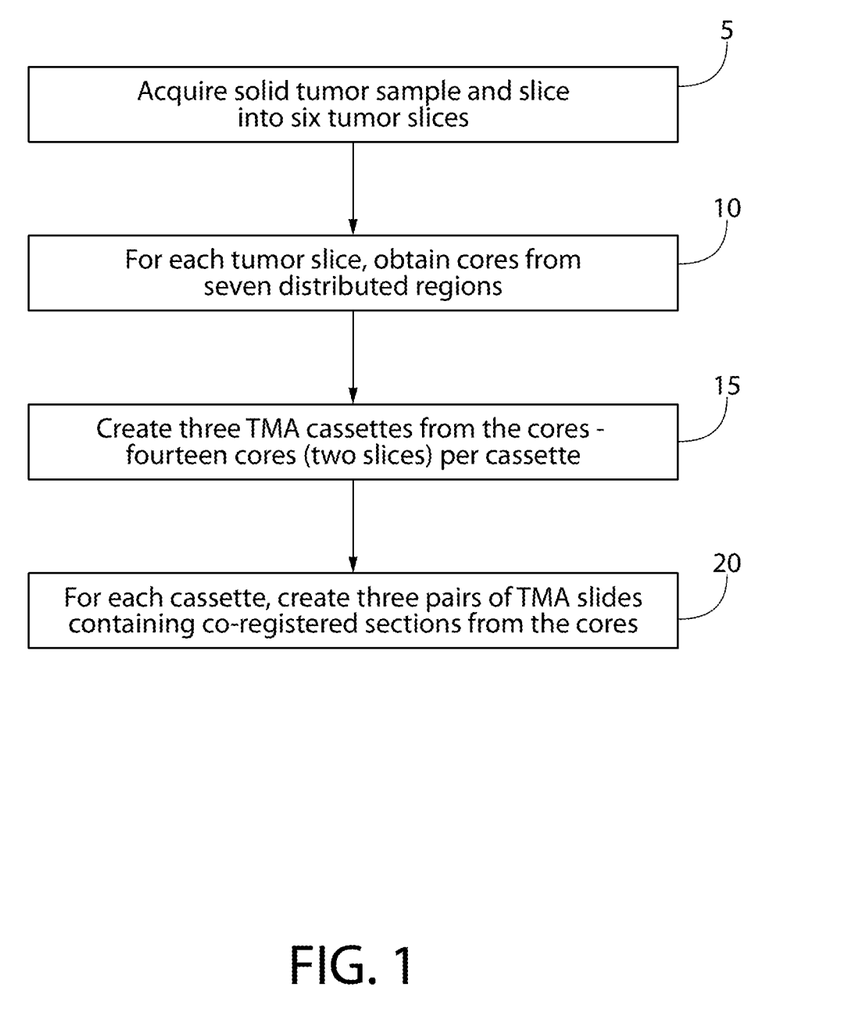
FIG. 1 is a flowchart illustrating a sample preparation methodology according to an exemplary embodiment of an aspect of the disclosed concept.
Figure 2:
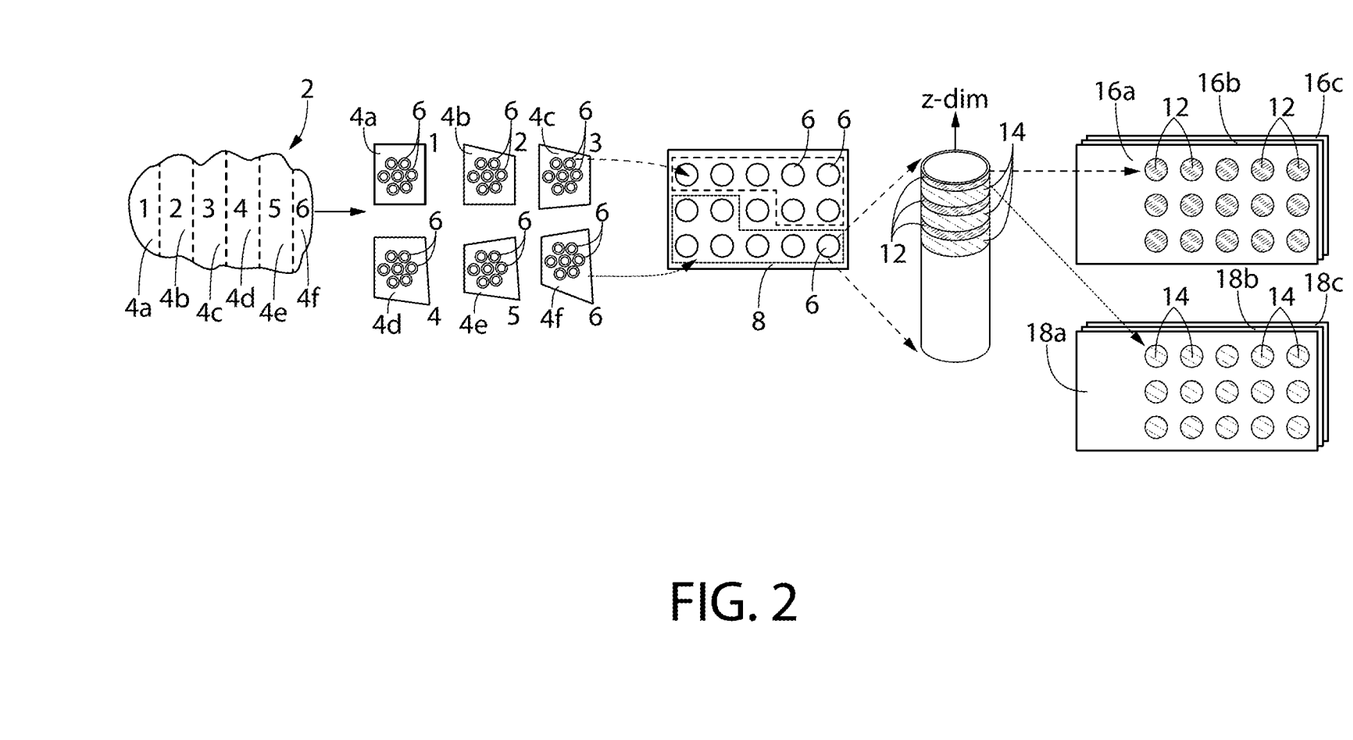
FIG. 2 is a schematic diagram illustrating the sample preparation methodology shown in FIG. 1.

FIG. 1 is a flowchart and FIG. 2 is a schematic diagram illustrating a sample preparation methodology according to an exemplary embodiment of an aspect of the disclosed concept. As described herein, the sample preparation methodology illustrated in FIGS. 1 and 2 provides a plurality of tissue samples that may then be used to generate the SCORGI data elements as described herein.

Referring to FIGS. 1 and 2, the methodology begins at step 5, wherein a solid tumor sample 2 as shown in FIG. 2 is acquired. In the non-limiting, exemplary embodiment, tumor sample 2 is on the order of 1.5 cm². Also in step 5, solid tumor sample 2 is sliced into six individual tumor slices 4, labeled 4a-4f in FIG. 2. In the exemplary embodiment, tumor slices 4a-4f are processed into formalin-fixed paraffin-embedded (FFPE) slices. Next, at step 10, seven individual core samples or "cores," each labeled 6 in FIG. 2, are obtained from distributed regions in each of the tumor slices 4a-4f. In the non-limiting exemplary embodiment, each core 6 is a large bore 5 mm core. Thus, following step 10, a total of forty-two cores 6 will have been acquired from tumor slices 4a-4f.

Next, at step 15, the forty-two cores 6 are used to create three large bore tissue microarray (TMA) cassettes 8, one of which is shown in FIG. 2. As seen in FIG. 2, each TMA cassette 8 will include the seven cores 6 from a respective two of the tissue tumor slices 4a-4f (e.g., the first TMA cassette 8 may include the cores 6 obtained from tumor slices 4a and 4b, the second TMA cassette 8 may include the cores 6 obtained from tumor slices 4c and 4d, and the third TMA cassette 8 may include the cores 6 obtained from tumor slices 4e and 4f).

Then, the methodology proceeds to step 20, wherein in the present non-limiting, exemplary embodiment, each TMA cassette 8 is used to create three pairs of TMA slides (for a total of nine pairs of TMA slides) that contain a plurality of pairs of co-registered and co-positioned sections from the cores 6. More specifically, as shown in FIG. 2, in the non-limiting, exemplary embodiment, three imaging data sections 12 and three genomic data sections 14 are obtained from each core 6 in each TMA cassette 8. In the non-limiting, exemplary embodiment, each imaging data section 12 is a 5 μm thick, 5 mm diameter tissue section, and each genomic data section 14 is a 10-20 μm thick, 5 mm diameter tissue section (genomic data sections 14 are, in the exemplary embodiment, thicker than imaging data sections 12 because typically more tissue is required for the genomic analysis that is to be performed on genomic data sections 14 than is required for the imaging that is to be performed on imaging data sections 12 as described herein). As seen in FIG. 2, the three imaging data sections 12 and the three genomic data sections 14 are obtained from each core 6 in an alternating fashion such that each imaging data section 12 will be directly adjacent to a genomic data section 14 so that they form sequential/serial pairs of adjacent tissue sections (i.e., SCORGI tissue sections) that may, as described herein, be used to create a plurality of SCORGI data elements. Thus, in the present, non-limiting exemplary embodiment, a total of forty-two imaging data sections 12 and a total of forty-two genomic data sections 14 are obtained from the fourteen cores 6 that are provided on each TMA cassette 8. Accordingly, for the three TMA cassettes 8 of the exemplary embodiment, a total of one hundred twenty-six imaging data sections 12 and a total of one hundred twenty-six genomic data sections 14 are obtained.

In addition, as seen in FIG. 2, for each TMA cassette 8, the obtained imaging data sections 12 are sequentially positioned on three imaging data TMA slides 16a, 16b, 16c, and the obtained genomic data sections 14 are sequentially positioned on three genomic data TMA slides 18a, 18b, 18c. As a result, the three pairs of TMA slides described above are formed for each TMA cassette 8, wherein the first pair comprises an imaging data TMA slide 16a and a genomic data TMA slide 18a, the second pair comprises an imaging data TMA slide 16b and a genomic data TMA slide 18b, and the third pair comprises an imaging data TMA slide 16c and a genomic data TMA slide 18c. In addition, as will be appreciated, for each TMA cassette 8, each pair of TMA slides will include fourteen pairs of co-registered imaging data sections 12 and genomic data sections 14, with the imaging data sections 12 being provided on the TMA slides 16 and the corresponding genomic data sections 14 being provided on corresponding locations on the TMA slides 18. Thus, at the completion of step 20, a total of nine pairs of TMA slides (nine TMA slides 16 and nine TMA slides 18)

will have been formed from the three TMA cassettes 8 of the present embodiment, resulting in a total of one hundred twenty-six co-registered and co-positioned pairs of imaging data sections 12 and genomic data sections 14 (i.e., one hundred twenty-six SCORGI tissue sections). As noted above, it is those co-registered and co-positioned pairs of imaging data sections 12 and genomic data sections 14 that may be used to create a plurality of data elements referred to as SCORGIs as described herein.

It should be noted that the exemplary numbers of the various items described above, e.g., the number of (e.g., six) tumor slices 4, the number of (e.g., seven) cores 6 from each tumor slice 4, and the number of (e.g., three), diameter and/or thickness of imaging data sections 12 and genomic data sections 14 from each core 6, are meant to be exemplary only, and that other numbers of such items are contemplated within the scope of the disclosed concept. For example, and without limitation, the size of the core for multi to hyperplexed imaging as described herein can be larger than the 5 mm. Specifically, tumors are typically centimeters across (e.g., 1-5 cm), and the entire tumor could be sectioned to create 1-5 cm diameter sections within the scope of the disclosed concept. In such an implementation, a whole slide image (WSI) of the sections could be made and multi to hyperplexed imaging of the WSI could be performed.

Figure 3:
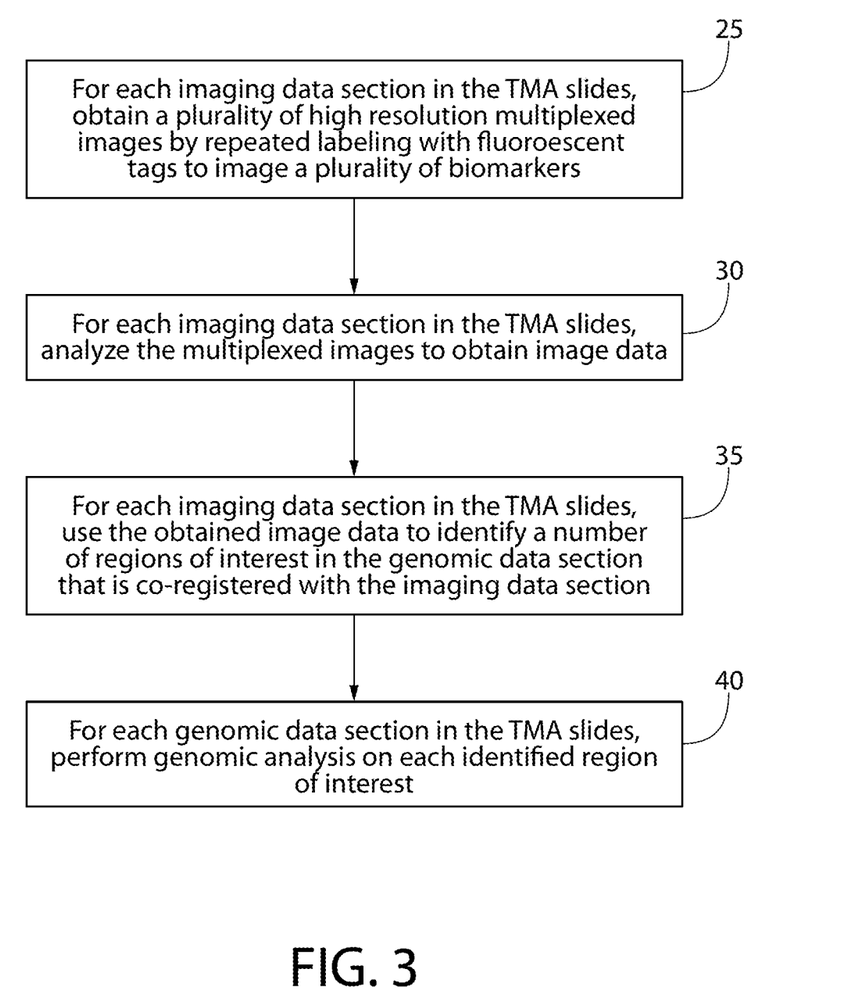
FIG. 3 is a flowchart illustrating a method for generating SCORGI data elements from the co-registered and co-positioned pairs of imaging data sections and genomic data sections according to an exemplary embodiment of a further aspect of the disclosed concept.
Figure 4:
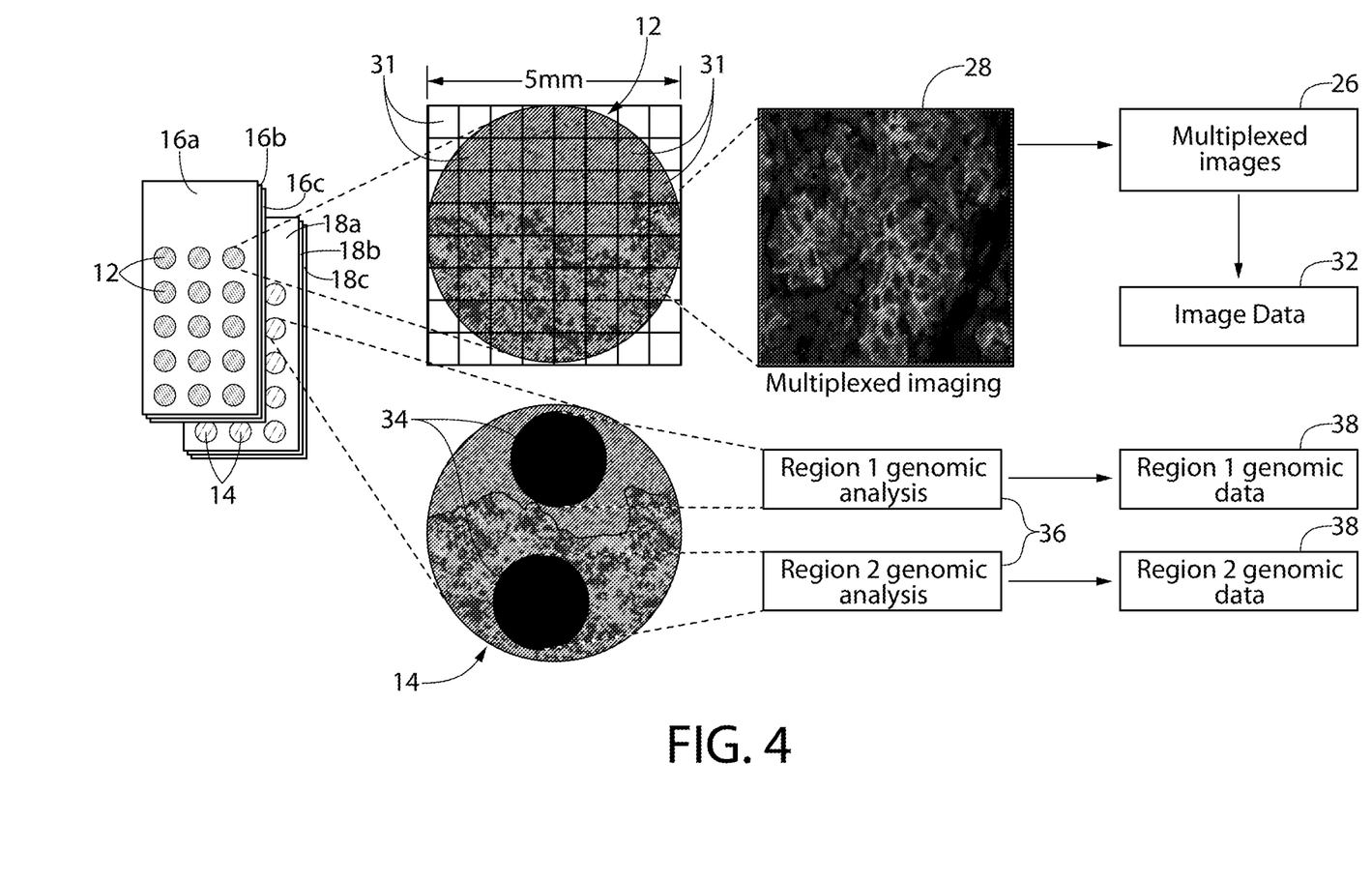
FIG. 4 is a schematic diagram illustrating the method for generating SCORGI data elements of FIG. 3.

FIG. 3 is a flowchart and FIG. 4 is a schematic diagram illustrating a method for generating SCORGI data elements from the co-registered and co-positioned pairs of imaging data sections 12 and genomic data sections 14 (referred to herein as SCORGI tissue sections) according to an exemplary embodiment of a further aspect of the disclosed concept. In particular, as described in more detail below, the SCORGIs are generated by performing multi to hyperplexed imaging and region-specific genomics on each of the co-registered and co-positioned pairs of imaging data sections 12 and genomic data sections 14, respectively.

Referring to FIGS. 3 and 4, the method begins at step 25, wherein, for each imaging data section 12 in TMA slides 16a, 16b, and 16c, a plurality of high resolution multi to hyperplex images 26 are generated from the imaging data section 12 using a multi to hyperplexed imaging process 28 that, in the exemplary embodiment, includes repeated labeling of each imaging data section 12 with a plurality of fluorescent tags to image a plurality of biomarkers. In the illustrated exemplary embodiment, as shown in FIG. 4, each imaging data section 12 is divided into sixty image fields 31, fifty different fluorescent tags are applied to the imaging data section 12, and an image 26 is captured (e.g., at 20×) for each fluorescent tag for each image field 28. As a result, in this exemplary embodiment, a total of 3,000 multi to hyperplexed images 26 will be captured for each imaging data section 12. It will be appreciated that the number and selection of biomarkers used in step 25 may vary and may depend on the mechanisms of tumor progression of interest.

Next, at step 30, for each imaging data section 12 in the TMA slides 16a, 16b, and 16c, the generated multi to hyperplexed images 26 are analyzed in order to obtain image data 32 as shown FIG. 4. In particular, the fluorescent multi to hyperplexed images 26 for each field 31 contain intensity distributions for each biomarker. Thus, in the exemplary embodiment, the multi to hyperplexed images 26 are processed to extract image data 32 that comprises a quantification of information extracted from the multi to hyperplexed images 26. Such image data 32 may include, without limitation, quantifications such as subcellular biomarker intensities and localization in each cell for each multi to hyperplexed image 26, morphometrics like size and shape of cells or subcellular regions, and/or intensity distributions in cells or subcellular regions which could be characterized by statistical measures or texture measures.

In the exemplary embodiment, a standard multiplexing machine, such as the PerkinElmer Vectra Polaris Automated Quantitative Pathology System (http://www.perkinelmer.com/product/vectra-polaris-top-level-assembly-ship-cls143455), may be used to generate the multiplexed images 26 and the image data 32 as just described (in such a case, the standard multiplexing machine typically includes software for generating the image data 32). Alternatively, a standard multiplexing machine as just described may be used to generate the multiplexed images 26, and the image data 32 may be generated therefrom using separate image analysis software, such as, without limitation, the public domain THRIVE (Tumor Heterogeneity Research Interactive Visualization Environment) software described in Spagnolo, et al., *Platform for Quantitative Evaluation of Spatial Intratumoral Heterogeneity in Multiplexed Fluorescence Images*, Cancer Res. 2017 Nov. 1; 77(21):e71-e74. The THRIVE software is an open-source tool for assisting cancer researchers in interactive hypothesis testing. THRIVE provides an integrated workflow for multi to hyperplexed analysis of whole slide immunofluorescence images and tissue microarrays, including standard cell and subcellular segmentation and biomarker quantification. THRIVE quantifies spatial intratumoral heterogeneity, and the interactions between different cell phenotypes and non-cellular constituents. THRIVE is capable of deciphering diverse molecular and cellular signaling networks supporting the reciprocal coevolution of malignant cells and their specific TME (e.g., cancer associated fibroblasts, immune cells, extracellular matrix) to confer malignant phenotypes resulting in, for example, dormancy, drug resistance, immune evasion, and metastatic potential.

As still a further alternative, the generation of hyperplexed images 26 and the image data 32 from TMA slides 16a, 16b, and 16c as just described may be generated by sending TMA slides 16a, 16b, and 16c to a hyperplexing immunofluorescence Clinical Laboratory Improvement Amendments (CLIA) lab, such as the NeoGenomics MxIF: Multi-molecular multiplexing methodology lab (https://neogenomics.com/pharma-services/lab-services/multiomyx), among others.

Following step 30, the method proceeds to step 35, wherein, for each of the imaging data sections 12 in the TMA slides 16a, 16b, and 16c, the obtained image data 32 is used to identify a number of regions-of-interest ("ROIs", also referred to as "microdomains") in the genomic data section 14 (contained in one TMA slides 18a, 18b, and 18c) that is co-registered with the imaging data section 12. The ROIs may be identified using the obtained image data 32 according to any of a number of known or hereafter developed methodologies such as, without limitation, the methodology that is described in detail in U.S. provisional application Ser. No. 62/675,832, filed on May 24, 2018 and entitled "Predicting the Recurrence Risk of Cancer Patients From Primary Tumors with Multiplexed Immunofluorescence Biomarkers and Their Spatial Correlation Statistics," incorporated herein by reference, in PCT Application No. PCT/US19/033662, filed on May 23, 2019 and entitled "Predicting the Recurrence Risk of Cancer Patients From Primary Tumors with Multiplexed Immunofluorescence Biomarkers and Their Spatial Correlation Statistics," incorporated herein by reference, and in Spagnolo, et al., Platform for Quantitative Evaluation of Spatial Intratumoral Heterogeneity in Multiplexed Fluorescence Images, Cancer Res.

2017 Nov. 1; 77(21):e71-e74 and implemented in the THRIVE software. In that methodology, spatially resolved correlations between biomarkers as covariates in a multi-variable survival model of outcome data (e.g., recurrence) are used to build a map for the spatial organization of cancer recurrence in a hyperplexed tissue sample. These maps delineate microdomains associated with recurrence and metastatic progression. Additionally, it is expected that performing region-specific genomics on the phenotypically distinct microdomains of the SCORGI data elements as described herein will reveal enriched malignant cell sub-clonal populations that are also enriched in the metastases themselves. The integration of genomic and imaging information in SCORGIs as described herein enables modeling of phenotypic and genotypic progression and development of predictive biomarkers mechanistically linked to metastatic progression.

Referring again to FIG. 4, an exemplary genomic data section 14 and two exemplary ROIs 34 ("Region 1" and "Region 2") are shown. At step 40, for each of the genomic data sections 14 in TMA slides 18a, 18b, and 18c, genomic analysis, as identified by reference numeral 36, is performed for each identified ROI 34 in the genomic data section 14. As result of and based on the genomic analysis 36, genomic data 38 for each identified ROI 34 for each genomic data section 14 will be generated. For example, and without limitation, the genomic analysis that is performed in step 40 may be whole exome sequencing acquired via next generation sequencing methods, in situ transcriptomics, and epigenomics, among others, and the genomic data 38 that is generated may include, without limitation, data indicative of mutations and/or data indicative in situ transcriptomics (FISSEQ, DSP).

Step 40 as just described may be performed by any suitable methodology and/or apparatus. For example, DNA extraction from an ROI 34 may be performed using a microfluidic dissection method and unit that is compatible with standard optical microscopes for rapid extraction of nucleic acids from small (1-5 mm) ROIs of standard FFPE tissue sections that has been developed by, Neuroindx (http://www.neuroindx.com/). In this method, the location of the ROI is transferred to the microfluidic dissection unit and a microfluidic gasket is positioned tightly over the corresponding ROI. A tissue digestion buffer is then automatically pumped over the tissue and circulated within the ROI gasket. Once digested, the liquefied tissue sample (i.e., extracted ROI) is pumped back into a reservoir and then transferred into a tube. Thereafter, the DNA may be extracted from the tissue digests and quantified using standard Qiagen and Invitrogen reagents and protocols. For genomic analysis, next-generation sSequencing, such as whole-exome sequencing (WES), can be done by an external sequencing service provider such as the RPCI Genomic Shared Resource at the Roswell Park Cancer Institute, Buffalo, N.Y. For example, WES may be performed using SureSelect Human All Exon V6 plus COSMIC r2 (Design ID S07604715, ~64 Mbp) as target from Agilent. The raw reads received from such sequencing may be further analyzed using a pipeline assembled from publicly available software packages and/or custom software scripts.

In the exemplary embodiment, following step 40, the multi to hyperplexed images 26, the image data 32, and the genomic data 38 for each co-registered imaging data section 12 and genomic data section 14 (i.e., each SCORGI tissue section) are stored in association with one another (in a suitable computer readable storage medium such as those described herein) as a SCORGI data element. In the non-limiting, exemplary embodiment being described herein, one hundred twenty-six SCORGI data elements will be created and stored.

Figure 5:
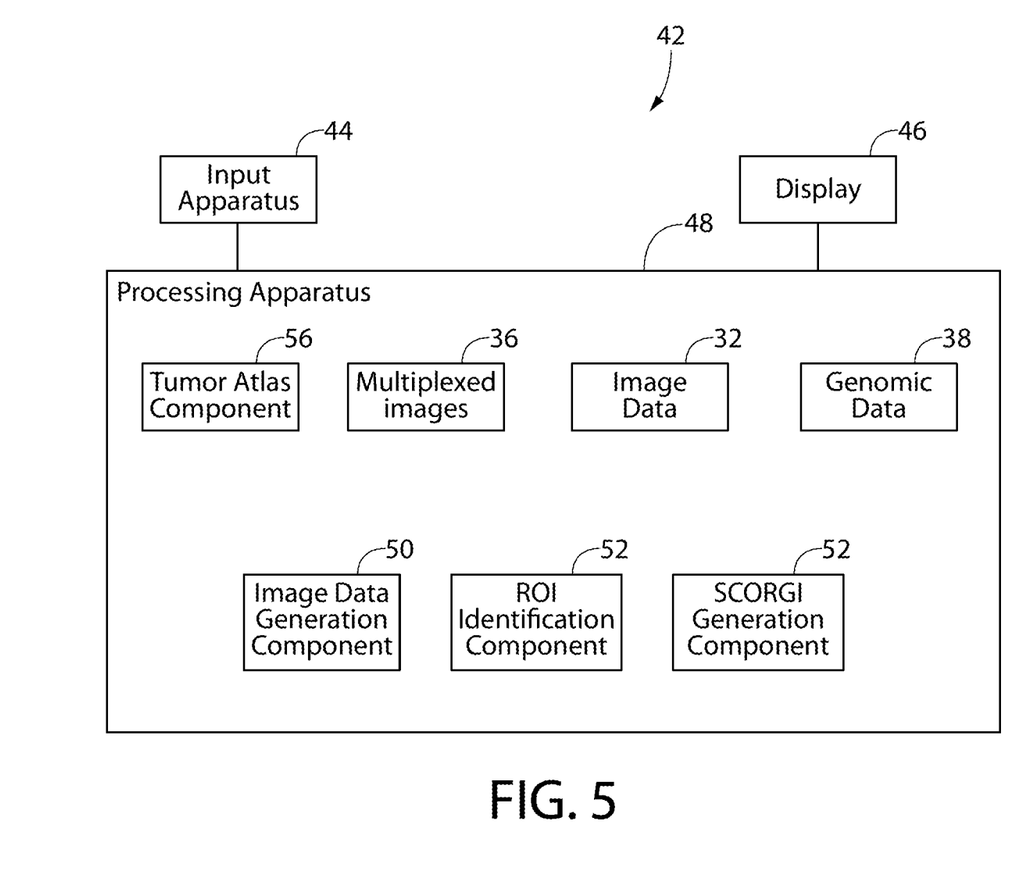
FIG. 5 is a schematic diagram of an exemplary digital pathology system according to one particular, non-limiting exemplary embodiment of the disclosed concept.

As noted elsewhere herein, in one particular embodiment, the disclosed concept may be implemented as part of a digital pathology system in a manner wherein the image data 32 is generated from the multi to hyperplexed images 26 and the ROIs in the genomic data sections 14 are identified using the obtained image data 32 using software tools, such as, without limitation, the THRIVE software described herein, that are local to or otherwise accessible by a local computing device forming a part of the digital pathology system. In addition, as also noted elsewhere herein, in such an embodiment, certain genomic data 38 may also be generated from raw sequencing data using software tools that are local to or otherwise accessible by the same computing device. FIG. 5 is a schematic diagram of such an exemplary system 42 according to one particular, non-limiting exemplary embodiment. As seen in FIG. 5, system 42 comprises a computing device that may be, for example and without limitation, a PC, a laptop computer, a tablet computer, or any other suitable device structured to perform the functionality described herein. System 42 may be located, for example and without limitation, in the same lab that performs the sampling as shown in FIGS. 1 and 2 and described herein. System 42 includes an input apparatus 44 (such as a keyboard and/or touchpad), a display 46 (such as an LCD), and a processing apparatus 48. A user is able to provide input into processing apparatus 48 using input apparatus 44, and processing apparatus 48 provides output signals to display 46 to enable display 46 to display information (e.g., SCORGI related information) to the user as described in detail herein.

Processing apparatus 48 of system 42 comprises a processor and a memory. The processor may be, for example and without limitation, a microprocessor (μP), a microcontroller, an application specific integrated circuit (ASIC), or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a non-transitory computer readable medium, for data storage such as in the fashion of an internal storage area of a computer, and can be volatile memory or nonvolatile memory. The memory has stored therein a number of routines that are executable by the processor, including routines for implementing various aspects of the disclosed concept as described herein. In particular, in the illustrated embodiment shown in FIG. 5, processing apparatus 48 is structured to receive and store the multi to hyperplexed images 26 as described elsewhere herein. Processing apparatus 48 further includes an image data generation component 50 that is structured and configured to generate the image data 32 (i.e., the quantifications) as described elsewhere herein from the received and stored multi to hyperplexed images 26. The generated image data 32 is then stored by processing apparatus 48. As noted above, image data generation component 50 may comprise the THRIVE software described elsewhere herein. In addition, processing apparatus also includes an ROI identification component 52 that is structured and configured to identify the ROIs in the genomic data sections 14 using the obtained image data 32 as described elsewhere herein. The identified ROIs may then be used to generate the genomic data 38 as described herein, which is then stored by processing apparatus 48. As also noted above, ROI identification component 52 may similarly comprise the THRIVE software described elsewhere herein.

In addition, as seen in FIG. 5, processing apparatus 48 of the present embodiment further includes a SCORGI generation component 54. SCORGI generation component 54 is structured and configured to generate and store the SCORGI data elements as described herein based on the stored multi to hyperplexed images 26, the image data 32, and the genomic data 38.

Figure 6:
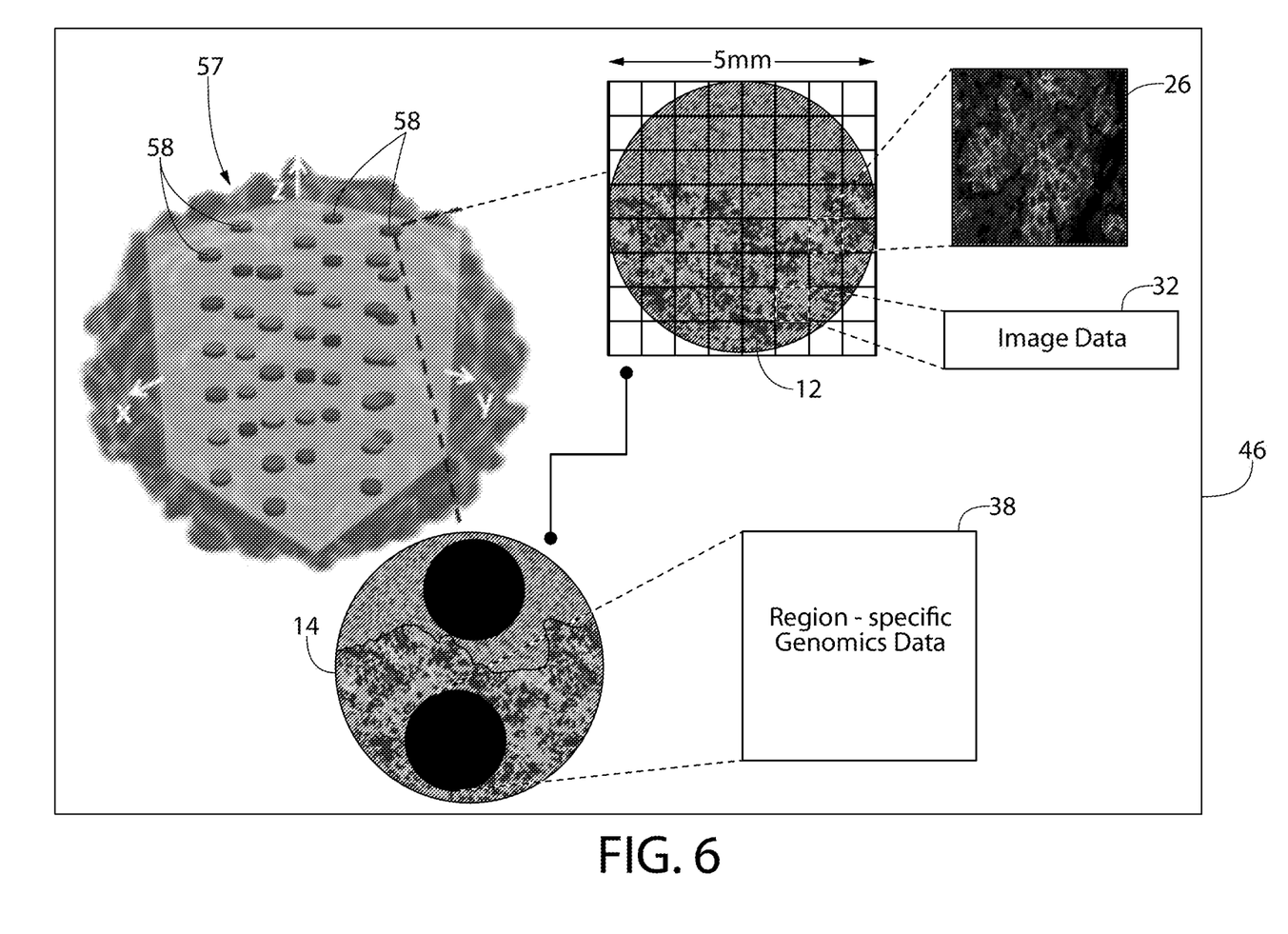
FIG. 6 is a schematic diagram illustrating the generation of a tumor atlas according to one non-limiting aspect of the disclosed concept.

In addition, as also seen in FIG. 5, according to a further aspect of the present embodiment, processing apparatus 48 further includes a tumor atlas component 56. Tumor atlas component 56 is, according to one non-limiting aspect of the disclosed concept, structured and configured to generate and display on display 46 a tumor atlas 57 as shown in FIG. 6. Tumor atlas 57 is a three-dimensional (3D) map that is able to show spatial ITH by way of a plurality of SCORGI icons 58. Specifically, each SCORGI icon 58 represents and corresponds to a SCORGI data element that has been generated by SCORGI generation component 54 from a particular tissue sample or samples as described herein. As seen in FIG. 6, each SCORGI icon 58 is positioned as a specific location in the x, y, z coordinate system of tumor atlas 57. That particular location corresponds to and is based on the location within the original tissue sample of the particular the tissue sections that were used to generate the SCORGI data element to which the SCORGI icon 58 corresponds. In addition, tumor atlas component 56 is structured and configured to generate the tumor atlas 57 such that certain images and/or information are able to be selectively displayed on display 46 when a particular one of the SCORGI icons 58 is selected by a user using input apparatus 44. For example and without limitation, as seen in FIG. 6, the displayed information may include one or more of: (i) images of the imaging data sections 12, (ii) images of the genomic data sections 14, (iii) selected multi to hyperplexed images 26, (iv) selected portions of the image data 32, and (v) selected portions of the region specific genomics data 38.

Tumor atlas 57 as just described is just one application of the SCORGI based sampling of the disclosed concept. Other applications may include use of scRNAseq as a region-specific genomics procedure in SCORGI generation to establish phylogenetic relationships among microdomains and to generate pseudo-time tumor evolution trajectories within a given biospecimen and among longitudinally collected samples from the same patient (e.g., regional lymph nodes and distant metastases).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of creating a plurality of tissue sections for imaging and genomic analysis, comprising:
    obtaining a core from a tissue sample;
    obtaining from the core a plurality of imaging data sections and a plurality of genomic data sections in an alternating fashion along a length of the core such that each of the imaging data sections is associated with a respective one of the genomic data sections to form a plurality of serial pairs of adjacent tissue sections, wherein for each serial pair of tissue sections, the imaging data section and the genomic data section are obtained from immediately adjacent portions of the core along the length of the core; and
    fixing each of the imaging data sections from the core to a first tissue microarray (TMA) slide and fixing each of the genomic data sections from the core to a second tissue microarray (TMA) slide, wherein for each serial pair of tissue sections the imaging data section of the pair is fixed at a particular location on the first TMA slide and the genomic data section of the pair is fixed at a particular location on the second TMA slide that corresponds to and matches the particular location on the first TMA slide at which the imaging data section of the serial pair is fixed.

2. The method according to claim 1, wherein each imaging data section has a first thickness and each genomic data section has a second thickness that is greater than the first thickness.

3. The method according to claim 2, wherein the first thickness is 5 μm and the second thickness is 10-20 μm.

4. The method according to claim 1, wherein each imaging data section and each genomic data section has a diameter of 5 mm.

5. The method according to claim 1, wherein the tissue sample is a tumor, regional lymph node or distal metastases sample.

6. A plurality of tissue microarray (TMA) slides including tissue sections for imaging and genomic analysis, comprising:
    a first TMA slide having fixed thereto a plurality of imaging data sections for a core taken from a tissue sample; and
    a second TMA slide having fixed thereto a plurality of genomic data sections for each of the number of cores from the tissue sample;
    wherein the plurality of imaging data sections and the plurality of genomic data sections come from alternating portions along a length of the core such that each of the imaging data sections is associated with a respective one of the genomic data sections for the core to form a plurality of serial pairs of adjacent tissue sections, wherein for each serial pair of tissue sections, the imaging data section and the genomic data section are obtained from immediately adjacent portions of the core along the length of the core, and wherein for each serial pair of tissue sections the imaging data section of the pair is fixed at a particular location on the first TMA slide and the genomic data section of the pair is fixed at a particular location on the second TMA slide that corresponds to and matches the particular location of the first TMA slide at which the imaging data section of the serial pair is fixed.

7. The plurality of TMA slides according to claim 6, wherein each imaging data section has a first thickness and each genomic data section has a second thickness that is greater than the first thickness.

8. The plurality of TMA slides according to claim 7, wherein the first thickness is 5 μm and the second thickness is 10-20 μm.

9. The plurality of TMA slides according to claim 6, wherein each imaging data section and each genomic data section has a diameter of 5 mm.

10. The plurality of TMA slides according to claim 6, wherein the tissue sample is a tumor, regional lymph node or distal metastases sample.

11. A method of generating a plurality of spatially co-registered data elements from a tissue sample, comprising:
  obtaining a core from the tissue sample;
  obtaining from the core a plurality of imaging data sections and a plurality of genomic data sections in an alternating fashion along a length of the core such that each of the imaging data sections is associated with a respective one of the genomic data sections to form a plurality of serial pairs of adjacent, co-registered tissue sections, wherein for each serial pair of co-registered tissue sections, the imaging data section and the genomic data section are obtained from immediately adjacent portions of the core along the length of the core;
  fixing each of the imaging data sections from the core to a first tissue microarray (TMA) slide and fixing each of the genomic data sections from the core to a second tissue microarray (TMA) slide, wherein for each serial pair of co-registered tissue sections the imaging data section of the pair is fixed at a particular location on the first TMA slide and the genomic data section of the pair is fixed at a particular location on the second TMA slide that corresponds to and matches the particular location on the first TMA slide at which the imaging data section of the serial pair is fixed;
  for each of the imaging data sections: (i) obtaining a plurality of multi to hyperplexed images from the imaging data section by repeated labeling with a plurality of fluorescent tags, (ii) analyzing the multi to hyperplexed images to obtain image data therefrom, and (iii) identifying a number of regions of interest in the genomic data section associated with the imaging data section based on the obtained image data for the imaging data section;
  for each of the genomic data sections, performing genomic analysis on each of the regions of interest in the genomic data section to generate genomic data for the genomic data section; and
  for each serial pair of co-registered tissue sections, associating with one another as a co-registered imaging and genomic data element: (i) the multi to hyperplexed images of the imaging data section of the serial pair of co-registered tissue sections, (ii) the image data of the imaging data section of the serial pair of co-registered tissue sections, and (iii) genomic data of the genomic data section of the serial pair of co-registered tissue sections.

12. The method according to claim 11, further comprising storing the co-registered data imaging and genomic element for each co-registered tissue section in a non-transitory computer readable medium.

13. The method according to claim 11, further comprising generating and displaying on a display of a computer system a map comprising a plurality of co-registered data element icons, each co-registered data element icon being associated with and based on a respective one of the co-registered imaging and genomic data elements.

14. The method according to claim 13, further comprising, responsive to a selection of a particular one of the co-registered data element icons, causing one or more of a number of the multi to hyperplexed images, at least a portion of the image data, and at least a portion of the genomic data of the co-registered imaging and genomic data element associated with the particular one of the co-registered data element icons to be displayed on the display.

15. The method according to claim 11, wherein for each of the imaging data sections, the imaging data section is divided into a plurality of fields and the obtaining the plurality of multi to hyperplexed images by repeated labeling with the plurality of fluorescent tags comprises obtaining multiple images for each of the fields.

16. A non-transitory computer readable medium storing a plurality of spatially co-registered data elements generated according to the method of claim 11.

17. A non-transitory computer readable medium storing a plurality of spatially co-registered data elements generated according to the method of claim 14.

18. The non-transitory computer readable medium according to claim 17, wherein in each spatially co-registered data element, the genomic data is generated from a number of regions of interest in the genomic data section of the associated pair of co-registered tissue sections that are identified based on the image data generated from the plurality of multi to hyperplexed images obtained from the imaging data section of the associated pair of co-registered tissue sections.

19. A method of generating a plurality of spatially co-registered data elements from a tissue sample, the method comprising
  obtaining a core from the tissue sample:
  obtaining from the core a plurality of imaging data sections and a plurality of genomic data sections in an alternating fashion along a length of the core such that each of the imaging data sections is associated with a respective one of the genomic sections to form a plurality of serial pairs of adjacent, co-registered tissue sections, wherein for each serial pair of co-registered tissue sections, the imaging data section and the genomic data section are obtained from immediately adjacent portions of the core along the length of the core,
  fixing each of the imaging data sections from the core to a first tissue microarray (TMA) slide and fixing each of the genomic data sections from the core to a second tissue microarray (TMA) slide, wherein for each serial pair of co-registered tissue sections the imaging data section of the pair is fixed at a particular location on the first TMA slide and the genomic data section of the pair is fixed at a particular location on the second TMA slide that corresponds to and matches the particular location on the first TMA slide a which the imaging data section of the serial pair is fixed;
  for each serial pair of co-registered tissues sections: (i) obtaining and storing as part of a data element a plurality of multi to hyperplexed images obtained from the imaging data section of the serial pair of co-registered tissue sections, (ii) generated and storing image data obtained from the plurality of multi to hyperplexed images as part of the data element, and (iii) generating and storing genomic data obtained from the genomic data section of the serial pair of co-registered tissue sections as part of the data element.

20. The method according to claim 19, wherein for each pair of co-registered tissue sections, the genomic data is generated from a number of regions of interest in the genomic data section of the associated pair of co-registered tissue sections that are identified based on the image data generated from the plurality of multi to hyperplexed images obtained from the imaging data section of the associated pair of co-registered tissue sections.

21. The method according to claim 1, wherein each imaging data section and each genomic data section has a diameter of 1 cm to 5 cm.

22. A system for generating and storing a plurality of spatially co-registered data elements from a plurality of imaging data sections and a plurality of genomic data sections obtained from a core of a tissue sample in an alternating fashion along a length of the core such that each of the imaging data sections is associated with a respective one of the genomic data sections to form a plurality of serial pairs of adjacent, co-registered tissue sections, wherein for each serial pair of co-registered tissue sections, the imaging data section and the genomic data section are obtained from immediately adjacent portions of the core along the length of the core, wherein each of the imaging data sections from the core is fixed to a first tissie microarray (TMA) slide and each of the genomic data sections from the core is fixed in a second array microarray (TMA) slide, wherein for each serial pair of co-registered tissue sections the imaging data section of the pair is fixed at a particular location on the first TMA slide and the genomic data section of the pair is fixed at a particular location on the second TMA slide that corresponds to and matches the particular location on the first TMA slide at which the imaging data section of the serial pair is fixed, the system comprising a processing apparatus including:

an image data generation component that is structured and configured to generate for each serial pair of co-registered tissue sections image data from a plurality of multi to hyperplexed images obtained from the imaging data section of the serial pair of co-registered tissue sections;

a region of interest identification component that is structured and configured to identify for each serial pair of co-registered tissue sections a number of regions of interest in the genomic data section of the serial pair of co-registered tissue sections based on the generated image data of the serial pair of co-registered tissue sections, wherein for each serial pair of co-registered tissue sections genomic data is generated from the genomic data section of the serial pair of co-registered tissue sections based on the identified number of regions of interest; and a data element generation component that is structured and configured to generate and store for each pair of co-registered tissue sections a spatially co-registered data element of the plurality of spatially co-registered data elements, the stored spatially co-registered data element including the plurality of multi to hyperplexed images, the generated image data, and the generated genomic data of the serial pair of co-registered tissue sections.

23. The system according to claim 22, the processing apparatus further comprising a map generation component that is structured and configured to generate a map comprising a plurality of co-registered data element icons, wherein each of the co-registered data element icons is associated with and based on one of the spatially co-registered data elements generated by the data element generation component.

24. The system according to claim 23, wherein the processing apparatus is structured and configured to, responsive to selection of the one of the co-registered data element icons, cause one or more of the multi to hyperplexed images of the spatially co-registered data element, at least a portion of the generated image data of the spatially co-registered data element, and at least a portion of the generated genomic data of the spatially co-registered data element to be displayed.

* * * * *

UNITED STATES PATENT AND TRADEMARK OFFICE
CERTIFICATE OF CORRECTION

PATENT NO. : 12,033,726 B2
APPLICATION NO. : 17/265954
DATED : July 9, 2024
INVENTOR(S) : Srinivas C. Chennubhotla et al.

It is certified that error appears in the above-identified patent and that said Letters Patent is hereby corrected as shown below:

In the Claims

Column 14, Claim 19, Line 44:
Add the word --data-- after the word "genomic"

Column 14, Claim 19, Line 62:
Change the word "tissues" to --tissue-- before the word "sections: (i)"

Column 15, Claim 22, Line 28:
Change the word "tissie" to --tissue-- before the word "microarray"

Column 15, Claim 22, Line 30:
Delete the word "array" and add the word --tissue-- before "microarray"

Signed and Sealed this
Eighth Day of October, 2024

Katherine Kelly Vidal
*Director of the United States Patent and Trademark Office*